United States Patent [19]

Diana et al.

[11] Patent Number: 4,760,201
[45] Date of Patent: Jul. 26, 1988

[54] PROCESS FOR RECOVERING ALCOHOLS FROM SULFURIC ACID STREAMS (CS-342)

[75] Inventors: William D. Diana, Belle Mead; David L. Wernick, Elizabeth, both of N.J.

[73] Assignee: Exxon Research & Engineering Co., Florham Park, N.J.

[21] Appl. No.: 843,168

[22] Filed: Mar. 24, 1986

Related U.S. Application Data

[63] Continuation of Ser. No. 650,875, Sep. 17, 1984, abandoned.

[51] Int. Cl.[4] ................. C07C 29/86; C07C 31/12
[52] U.S. Cl. .................... 568/918; 568/886; 568/888; 568/889; 568/890
[58] Field of Search ............ 568/918, 888-890

[56] References Cited

U.S. PATENT DOCUMENTS

| | | | |
|---|---|---|---|
| 1,365,046 | 1/1921 | Ellis | 568/886 |
| 1,954,506 | 4/1934 | van Pesk et al. | 568/889 |
| 2,081,721 | 5/1937 | van Dijck et al. | 568/918 |
| 2,109,462 | 3/1938 | Burk et al. | 568/888 |
| 2,139,953 | 12/1938 | Guinot | 260/641 |
| 2,196,177 | 4/1940 | Burk et al. | 568/918 |
| 2,510,806 | 6/1950 | Egberts et al. | 508/918 |
| 2,535,069 | 12/1950 | Johnson | 568/918 |
| 3,349,107 | 10/1967 | Pawlenko | 260/410.9 |
| 3,527,790 | 9/1970 | Moundlic et al. | 568/889 |
| 4,538,010 | 8/1985 | Diana | 568/918 |

FOREIGN PATENT DOCUMENTS

| | | |
|---|---|---|
| 493884 | 10/1938 | Canada . |
| 506473 | 10/1954 | Canada . |
| 334228 | 9/1930 | United Kingdom ....... 568/889 |
| 411303 | 6/1934 | United Kingdom ....... 568/889 |
| 830369 | 3/1960 | United Kingdom ....... 568/889 |
| 998974 | 7/1965 | United Kingdom . |

OTHER PUBLICATIONS

N. Fefer and A. Rutkouski, J. Am. Oil Chemists' Soc., 45, 5 (1968).
H. Koch, Brenntstaff Chem., 36, 321 (1955).
C. L. Munson et al., Ind. Eng. Chem. Proc. Des. Dev., vol. 23, No. 1, pp. 109-115 (1984).
Newman, Steric Effects in Organic Chemistry, 1956, pp. 204-207.

Primary Examiner—J. E. Evans
Attorney, Agent, or Firm—J. B. Murray, Jr.; D. E. Furman

[57] ABSTRACT

According to the process of the present invention, alcohols are recovered from aqueous mixtures thereof with a concentrated strong acid by contacting such alcohol-containing aqueous concentrated acid mixtures with a carboxylic acid selected from the group consisting of acids of the formula $RCO_2H$ wherein R is a straight or branched-chain or cyclic alkyl of from 5 to 19 carbon atoms per molecule to form an extract phase containing the carboxylic acid in addition to said alcohol, and an aqueous raffinate phase depleted in the alcohol.

20 Claims, 2 Drawing Sheets

PROCESS FOR RECOVERING ALCOHOLS FROM SULFURIC ACID STREAMS (CS-342)

This is a continuation of application Ser. No. 650,875 filed 9/14/84, now abandoned.

BACKGROUND OF THE INVENTION

1. Field of the Invention

This invention relates generally to the recovery of alcohols from concentrated aqueous acid streams.

2. Description of the Prior Art

Large volumes of alcohols are produced annually by the catalytic hydration of olefins, in which the selected olefin feed is absorbed in a concentrated aqueous sulfuric acid stream to form the corresponding alcohol and alkyl ester of the sulfuric acid. For example, the absorption of butene to form sec-butanol and a sec-butyl ester of sulfuric acid can be illustrated by the following equation:

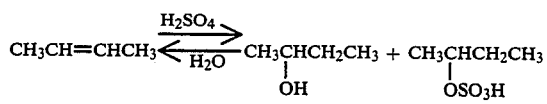

Thereafter, water is admixed with the sulfuric acid stream withdrawn from the absorber to hydrolyze the ester and to facilitate alcohol recovery which is accomplished by stripping with steam. There is thereby produced a diluted sulfuric acid stream which must for economic reasons be treated to concentrate it with respect to its sulfuric acid content, after which it is recycled to the olefin absorption step.

The reconcentration of the diluted sulfuric acid stream is a very expensive and energy-intensive process step, and a method whereby the alcohol could be recovered from the sulfuric acid stream withdrawn from the absorber, which did not require such a reconcentration, would be highly desirable.

Processes have been proposed for alcohol recovery by extraction from such alcohol-containing sulfuric acid streams by use of benzene, chloroform, ether, carbon bisulfide and toluene (U.S. Pat. No. 1,365,046); phenols, cresols, their homologues, ethers and phosphates (U.S. Pat. No. 2,139,953); and saturated hydrocarbons (British Pat. No. 493,884). British Pat. No. 506,473 relates to a method for production of organic oxy-compounds from a mixture of two liquid phases containing the oxy-compound distributed between the two layers in which the layers are separated and then recontacted at a lower temperature to extract the oxy-compound from the more hydrophobic phase, e.g., a hydrocarbon phase.

However, such extraction methods are not commercially desirable, since the solvents extract very little alcohol if the acid strength of the alcohol-containing sulfuric acid stream is greater than about 55%. Dilution of the acid stream to improve the ability of these solvents to extract the alcohol is not economically practicable, since even more expense would be incurred in reconcentrating the resulting sulfuric acid (recovered after the extraction) prior to its being recycled to the olefin absorbing step.

C. L. Munson et al., Ind. Eng. Chem. Proc. Des. Dev., vol. 23, no. 1, pp. 109-115 (1984) (which is not admitted herein to be prior art) investigated equilibrium distribution coefficients and separation factors for extraction of ethanol from dilute aqueous solutions of the alcohol by a number of different solvents and solvent mixtures, including extraction solvents comprising neodecanoic acid and 2-ethyl hexanoic acid. An ethanol-water-extraction solvent phase is obtained and treated to dehydrate the ethanol, followed by fractionating the ethanol and solvent mixture. The dilute aqueous raffinate is separated from the extractor and treated, as by stripping, to separate extraction solvent dissolved in the raffinate.

SUMMARY OF THE INVENTION

According to the process of the present invention, alcohols are recovered from aqueous mixtures thereof with a concentrated strong acid by contacting such alcohol-containing aqueous concentrated acid mixtures with a carboxylic acid selected from the group consisting of acids of the formula $RCO_2H$ wherein R is a straight or branched-chain or cyclic alkyl of from 5 to 19 carbon atoms per molecule to form an extract phase containing said carboxylic acid in addition to said alcohol, and an aqueous raffinate phase depleted in said alcohol.

It has been surprisingly found that the extraction solvents of this invention efficiently remove alcohol from concentrated aqueous strong acid solutions thereof and that the process permits recovery of this alcohol without substantial dilution of the aqueous strong acid. Thus, the recovered strong aqueous acid raffinate, depleted in alcohol, can be readily recycled, for example, directly to an olefin absorption process for absorption of additional olefin. Further, it has been surprisingly found that the extraction solvents of this invention permit only minor amounts of water to pass into the extraction solvent phase so that alcohol can be recovered substantially free of water. Finally, only minor quantities of the carboxylic acid extraction solvent have been found to pass into the aqueous raffinate in the process of this invention, thereby minimizing or avoiding the need to treat the raffinate for removal of the carboxylic acid extraction solvents.

DETAILED DESCRIPTION OF THE INVENTION

Prior Art Methods

Figure 1:
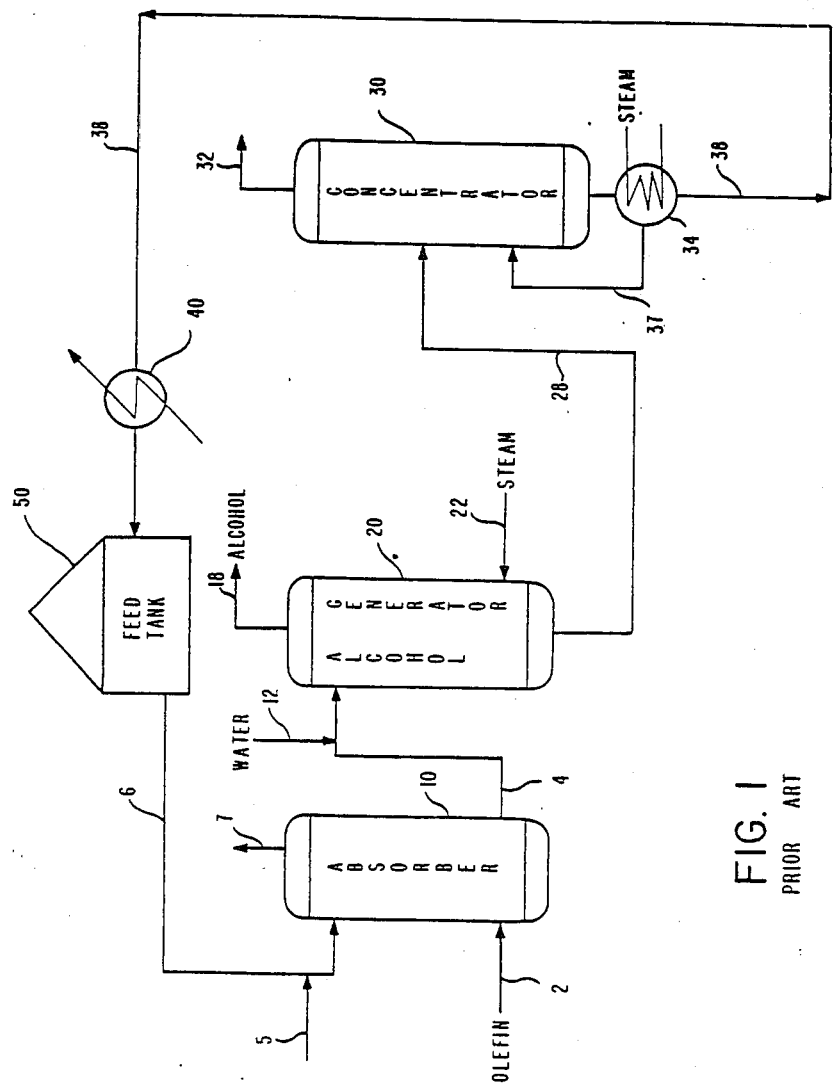
FIG. 1 is a diagrammatic illustration of a prior art process for indirect hydration of olefins using sulfuric acid, dilution of the sulfuric acid extract and stream stripping of the diluted acid for recovery of the alcohol vapors.

The prior art method of producing alcohols by hydrating the corresponding olefin can be illustrated by reference to FIG. 1. An olefin, for example an aliphatic olefin having from 2 to 8, and more typically from 2 to 4, carbon atoms per molecule (e.g., ethylene, propylene or butylene) is fed as a gas or liquid via line 2 to an absorber 10 wherein it is contacted with and absorbed (at least in part) by a concentrated aqueous strong acid stream introduced via line 6, to form the corresponding alcohol and alkyl ester of the strong acid. -P The olefins to be hydrated can be obtained from any available source, such as the destructive distillation of carbonaceous materials, but particularly from the cracking of petroleum hydrocarbons such as is practiced in the petroleum refining of mineral oils. The olefin can also be conventionally obtained by careful fractionation of cracked petroleum gases and is preferably substantially free of higher unsaturates, particularly diolefins such as butadiene, etc. Illustrative of olefins which are employed are lower branched and straight-chain alkenes (i.e., alkenes of 2 to 6 carbon atoms), such as ethylene, propylene, the butylenes and the like.

The strong acid used to absorb the olefin in absorber 10 (also termed "olefin hydration acid") will generally comprise a strong organic or inorganic acid which is miscible with water and which is characterized by dissociation constants ("pK" values) in aqueous solutions of less than about 3.5. Examples of suitable inorganic olefin hydration acids are hydrofluoric acid, hydroiodic acid, hydrochloric acid, ortho-phosphoric acid, phosphorous acid, perchloric acid, sulfuric acid and the like. Sulfuric acid is especially preferred. Examples of suitable organic olefin hydration acids are chloroacetic acid, benzene sulfonic acid and the like. For convenience, the following discussion will be directed to the use of sulfuric acid, although it will be understood that any of the above strong acids could also be employed.

The aqueous strong acid stream 6 of which is used to absorb the selected olefin feed is a concentrated acid stream whose precise acid concentration will vary depending on the olefin which is employed, the strong acid selected, the temperatures of reaction and other conditions. For example, when sulfuric acid is used as the strong acid, stream 6 will generally contain from about 45 to 99% acid strength sulfuric acid for hydration of propylene and from about 55 to 85% acid strength sulfuric acid for reaction with butylene or higher olefin feeds.

The temperature and pressure employed in absorber 10 generally also varies depending on the olefin, the acid concentration and other factors. Generally, a temperature of from about 20° to 150° C. is used, and the pressure is sufficient to maintain the desired liquid phases in the absorber. Typically, for example, propylene is absorbed from a gas phase at a temperature of from about 90° to 150° C., and at a pressure of from about 100-500 psig.

As illustrated, the olefin and sulfuric acid streams are contacted in a counter-current fashion with the sulfuric acid stream being introduced into the upper portion of the absorber 10. Unabsorbed gases are withdrawn from the upper portion of absorber 10 via conduit 7 and can be recycled, if desired, to conduit 2 or can be subjected to conventional scrubbing/washing treatment, as with caustic solutions. A product stream, comprising a sulfuric acid solution of the alcohol (herein termed the "absorber product stream"), is withdrawn via line 4 from the lower portion of absorber 10. The absorber product stream can also contain the alkyl ester corresponding to the selected olefin, e.g., diethyl sulfate when ethylene is the olefin, and di(isopropyl) sulfate in the case of propylene hydration. The concentration of the alkyl ester in stream 4 can vary widely, and is generally from 15 to 30 wt.% of the total alkyl ester (mono- and di-alkyl ester) in the case of lower alkenes (e.g., propylene and butylene) absorption.

In the second step of the hydration process, water is conventionally added via line 12 to the absorber product stream 4 for hydrolysis of any alkyl ester and to form additional quantities of the corresponding alcohol, e.g., isopropanol from mono- or di-(isopropyl) sulfate. The manner in which the water and absorber product stream are contacted varies, and the art employs a variety of such methods, including (1) in-line addition of water (as illustrated), with a provision for a suitable length of conduit to provide adequate mixing and reaction time, and (2) contacting of the absorber product stream and water in a separate reaction vessel with agitation (not shown).

The amount of water which is added to the absorber product stream also varies widely. Generally, sufficient water is added in order to reduce the acid strength to from 45% to 55% sulfuric acid. These reduced acid strengths are desired to permit subsequent recovery of the alcohol by steam stripping. Typically, from about 0.2 to 0.5 parts by weight of water is added per part by weight of the absorber product stream.

The diluted stream thus formed generally contains from about 45 to 55 wt.% sulfuric acid, and is then passed via line 4 to distillation column 20, herein termed the "alcohol generator," wherein crude alcohol is recovered as an overhead product via line 18 by steam stripping. The overhead alcohol product can then be passed to further conventional processing to produce alcohol of the required purity.

A bottoms product is withdrawn from alcohol generator 20 via line 28 and comprises a sulfuric acid stream which generally contains from about 40 to 55 wt.% sulfuric acid.

In conventional processes, the alcohol generator bottoms 28 are passed directly to another distillation column 30, hereinafter termed the "acid concentrator", wherein this acid stream is distilled (e.g., by use of a steam heat exchanger 34 and reboiled stream 37) for removal of water as overhead 32 and to form a second bottoms product 38 comprising a reconcentrated acid stream. These concentrated bottoms are generally cooled in cooler 40 and passed to storage tank 50 for ultimate recycle to the absorption step 10, with addition of make-up acid 5, as required.

Present Invention

Figure 2:
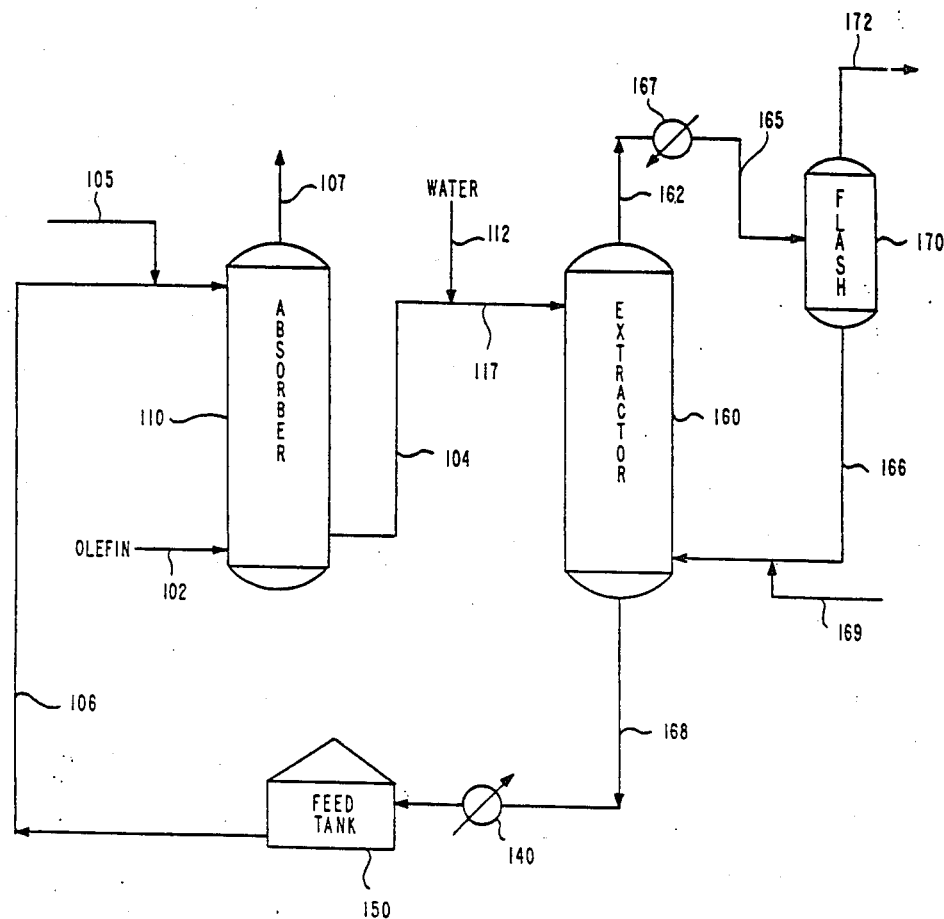
FIG. 2 is a diagrammatic illustration of one embodiment of the process of this invention.

Referring to FIG. 2, it has been surprisingly found that alcohols can be efficiently and quickly recovered by contacting a concentrated aqueous strong acid solution thereof 104 (herein termed the "acid/alcohol feedstream") with an effective amount of an extraction solvent 166 selected from the group consisting of alicyclic and acyclic alkyl carboxylic acids having from 6 to 20 carbon atoms per molecule. The carboxylic acids which are employed as extraction solvents 166 in the process of this invention therefore comprise at least one member selected from the group consisting of carboxylic acids of the formula:

wherein R is an alicyclic or acyclic alkyl group having from 5 to 19 carbon atoms. When "R" is acyclic alkyl, the alkyl group can be straight or branched chain. The "R" group can be substituted with nonreactive groups such as fluoro and chloro. Examples of such "R" groups are pentyl, hexyl, decyl, dodecyl, tetradecyl, undecyl, 2-ethylhexyl, cyclohexyl, cyclooctyl and fluoro- and chloro-substituted derivatives of the foregoing.

A preferred class of carboxylic acid extraction solvents for use in this invention comprise saturated acids, and especially saturated hindered acids wherein the carboxyl groups are sterically blocked or hindered. The discussion of steric hindrance may be found in Newman, Steric Effects in Organic Chemistry, 1956, pp. 204–207. Generally, steric hindrance results from the presence of tertiary or quaternary alpha, beta or gamma carbon atoms in the acid, increasing substitution leading to increased hindrance. Steric hindrance has been observed to tend to prevent esterification of the carboxylic acid with the alcohol.

A class of particularly preferred sterically hindered carboxylic acids are the neo acids ("neo" is used to denote a carbon atom that is bonded to four other carbon atoms, e.g., as in neo-hexanoic acid, i.e. 2,2-dimethyl butanoic acid). Thus, the preferred neo-acids can be represented by members selected from the group consisting of acids having the formula (II):

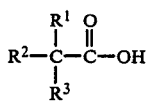

(II)

wherein $R^1$, $R^2$ and $R^3$ are the same or different and are independently selected from the group consisting of cyclic and alicyclic alkyl of from 1 to 16 carbon atoms, with the proviso that the neo acid contains a total of from 6 to 20 carbon atoms per molecule, and preferably from 7 to 15 carbon atoms per molecule. The alicyclic alkyl groups can be straight or branched. A preferred class of neo acids are those wherein, referring to formula II above, $R^1$ and $R^2$ are preferably each alkyl radicals having from 1 to 3 carbon atoms per radical and $R^3$ is preferably alkyl having from 1 to 6 carbon atoms, provided that the neo-acid has a total of at least 6, and preferably at least 7, carbon atoms per molecule.

Some typical examples of neo acids are 2,2-dimethyl butanoic acid; alpha, alpha-dimethyl cyclohexyl acetic acid; alpha, alpha-dimethyl octanoic acid, 1-methyl-4-propylcyclohexane-1-carboxylic acid; and the like.

Commercial neo-acids which comprise a mixture of isomers, all with the neo structure (formula II), such as neo-heptanoic acid, neo-octanoic acid, neo-nonanoic acid, neo-decanoic acid and neo-tridecanoic acid, are especially useful and preferred in the process of this invention. The preparation and properties of the commercial carboxylic acids are described in N. Fefer and A. Rutkouski, J. Am. Oil Chemists' Soc., 45, 5 (1968). Neo acids can also be prepared by the well known Koch process from carbon monoxide, water and type II, III, IV or V olefins as described by H. Koch in Brenntstaff Chem., 36, 321 (1955). Further details on methods for making neo acids can be found in British Pat. No. 998,974 and U.S. Pat. No. 3,349,107, all of which are hereby incorporated by reference. Neo acids are often made from branched chain olefin feedstocks which are random isomeric mixtures in regard to the position of the olefinic bond. These acids are thus random isomeric mixtures of neo acids. These neo acids are suitable in their isomeric forms, of any suitable mixtures thereof may be employed.

The carboxylic acid extraction solvent of this invention may be used alone or as mixtures with a cosolvent for the selected alcohol, such as a $C_{10}$ to $C_{20}$ paraffinic hydrocarbon, a $C_7$ to $C_{12}$ aromatic hydrocarbon, or a $C_1$ to $C_{10}$ alkyl ester of a $C_4$ to $C_{15}$ monocarboxylic acid. When used, such additional cosolvents will be generally employed in such mixtures in an amount of less than about 45 wt.% of the carboxylic acid/cosolvent mixture. In particular, it has been observed that the carboxylic acid extraction solvents of this invention, when contacted with alcohol and concentrated aqueous acid, will form the corresponding carboxylic ester of the alcohol, albeit at a rate which varies depending on the particular carboxylic acid extraction solvent selected for use. For example steric hindrance in the carboxylic acid, especially the neo structures (Structure II) will tend to reduce the rate and equilibrium constant of the esterification reaction. Eventually, the thus-formed ester of the carboxylic acid extraction solvent will build up to approximately a steady-state concentration in the continuous process in which the carboxylic acid extraction solvent is repeatedly recycled to extract additional quantities of alcohol from the alcohol-containing concentrated aqueous acid feedstream (as will be described in more detail below).

The selected carboxylic acid extraction solvent of this invention may be contacted with the acid/alcohol feedstream in extraction zone 160 in any convenient manner, including continuous, semi-continuous or batchwise operations, in a single or in multiple extraction stages. The concentration of the strong acid (e.g., sulfuric acid) in acid/alcohol feedstreams 104 (herein termed the "acid strength" or "A.S.") to be so contacted, can vary widely and will typically range from about 40 to 80 wt.% sulfuric acid, preferably from about 50 to 65 wt.% sulfuric acid when a neo acid is employed as the extracting solvent. As used herein, the acid strength in the acid/alcohol feedstream is defined herein on an organic free basis, as follows (using $H_2SO_4$ as the acid for purposes of illustration)

$$A.S. = \frac{W_1 + \left[\dfrac{M_1 \times W_4}{M_1 + M_5}\right]}{W_1 + W_2 + \left[\dfrac{18\ W_3}{M_3}\right] + \left[\dfrac{M_1 \times W_4}{M_1 + M_5}\right]} \times 100$$

wherein $W_1$ is the weight of strong acid, $W_2$ is the weight of $H_2O$, $W_3$ is the weight of alcohol, $W_4$ is the weight of the mono alkyl ester of the strong acid, $M_3$ is the molecular weight of the alcohol, $M_1$ is the molecular weight of the strong acid, and $M_5$ is the molecular weight of the olefin. Also, the concentrations of the alcohol and alkyl ester in the stream 104 can vary widely, and the saturated monoalcohol concentration will generally range from about 5 to 50 wt.% and preferably from about 10 to 40 wt.% and the saturated alcohol alkyl ester of the strong acid will generally range from about 1 to 15 wt.%, and preferably from about 1 to 5 wt.5, of total alkyl ester (mono- and di-alkyl ester).

The amount of carboxylic acid extraction solvent which is used to contact the acid/alcohol feedstream can also vary widely. Preferably, the carboxylic acid extraction solvent of this invention and the acid/alcohol feedstream are contacted in zone 160 in a ratio of from about 0.3 to 5 parts by weight of the carboxylic acid per part by weight of the acid/alcohol feedstream.

The temperature and pressure in zone 160 in which such extraction is performed using the carboxylic acid solvents of this invention is not critical, and will vary widely depending upon the particular carboxylic acid solvent employed, the degree of efficiency of removal desired for the alcohol, phase settling time desired, and other factors. Generally, however, temperatures within the range from about 25° to 100° C., preferably from about 25° to 80° C., can be used, and the pressure can be atmospheric, subatmospheric or superatmospheric, with pressures of from about 2 to 100 psig being typically suitable. Similarly, the time for the contacting of the selected carboxylic acid solvent of this invention and the acid/alcohol feedstream is not critical and can vary widely, but will typically fall within the range of from about 0.1 to 6 hours.

Finally, the process of this invention can employ as extraction zone 160, in which the extraction with carboxylic acid solvent is carried out, any of the conventional equipment which are employed for liquid-liquid extractions. For example, the solvent and the acid/alcohol feedstream can be introduced as a combined stream into a stirred tank, and the resulting liquids passed to a settling drum from which the light phase (alcohol solvent phase) and the heavy phase (lean acid-/alcohol phase) can be recovered. Alternatively, the contacting zone can comprise a static plate extraction column (either packed or trayed column), a reciprocating plate column (such as the KARR® column), stirred columns (such as YORK-SCHIEBEL® columns) and the like.

In the process of this invention, water may be added to the acid/alcohol feedstream 104 in order to provide the water of hydration for formation of the selected alcohol from alkyl ester corresponding to the alcohol. This water can be introduced via stream 112 into the conduit carrying the acid/alcohol feedstream 104 as illustrated, or the water can be introduced into zone 160 itself. Generally, from about 0.04 to 0.4 parts by weight of water are added per part by weight of the acid/alcohol feedstream.

An alcohol-rich carboxylic acid extract stream 162 can be thus separated and recovered as the light phase from extraction zone 160, either directly from zone 160 (as illustrated) or following treatment of a two-phase mixture removed from the contacting zone to a conventional phase separation vessel. This alcohol-rich carboxylic extract 162 generally contains from about 5 to 20 wt.% alcohol and from about 95 to 45 wt.% of the carboxylic acid solvent. The alcohol-rich carboxylic acid extract 162 will only contain a minor proportion of water, preferably less than about 2 wt.% water, more preferably less than about 1 wt.% water, and most preferably less than about 0.3 wt.% water. In addition, it has been found that the carboxylic acid extraction solvents of this invention permits recovery of such a alcohol-rich stream without, at the same time, contamination with significant amounts of the strong acid or alkyl ester of the strong acid. Generally, the alcohol-rich carboxylic acid extract 162 recovered from the contacting zone contains less than about 1 wt.%, most preferably less than about 0.3 wt.%, of such alkyl esters and is substantially free of the strong acid, that is, contains less than 0.1 wt.% and most preferably less than 0.01% wt.%, of the strong acid (e.g., $H_2SO_4$).

A second phase 168 can also be recovered, again either directly or indirectly, from the extraction zone 160 as the heavy phase and comprises a mixture of water, strong acid and alkyl moieties, either as the monoester or di-ester of the strong acid or the alcohol, or mixtures thereof, enriched in the strong acid. This separated strong acid-enriched phase 168 can be recycled to an olefin absorbing zone 110, after addition of make-up strong acid 105, if required. Generally, this strong acid phase 168 separated from the extraction zone 160 will contain strong acids in an acid strength of at least 1 wt.%, and preferably from about 2 to 10 wt.% greater than the acid strength of the strong acid in the diluted acid/alcohol feedstream 117 passed to extraction zone 160.

Preferably, the extraction process of this invention is performed by continuouly passing the acid/alcohol feedstream 117 and the carboxylic acid extraction solvent 166 to the extraction zone 160 countercurrently, and at flow rates such that the strong acid phase, that is the acid/alcohol feedstream 117, is the discontinuous phase and is introduced to the upper portion of the extraction tower 160, with the extraction solvent phase comprising the continuous phase. It has been found that such an embodiment greatly reduces the time required for phase separations to occur during the extraction.

The alcohol rich carboxylic acid extract 162 can then be treated for recovery of the alcohol therefrom and for recovery and separation of the carboxylic acid solvent for recycle, if desired to the extraction zone 160 in order to extract additional quantities of alcohol therein. The manner in which the alcohol is removed from this alcohol enriched phase can vary widely, and can include steam stripping or the use of the alcohol recovery methods described in Ser. No. 650,874, filed Sept. 17, 1984, now U.S. Pat. No. 4,538,010 (the disclosure of which is hereby incorporated by reference), which methods include distillation, flashing, or stripping using a substantially anhydrous gas which is inert to the alcohol and extraction solvent under stripping conditions, such as $N_2$, and olefins and paraffins of 2–8 carbons, e.g., butene, butane, and the like. For example, the separated alcohol-enriched carboxylic acid extract phase 162 can be heated (e.g., using heat exchanger 167) to a temperature of from about 0° to 200° C. higher than the temperature employed in extraction zone 160, and the resulted heated alcohol-enriched stream 165 can be flashed into a vapor/liquid separation zone 170 (such as a suitable vapor/liquid separating drum) at a lower pressure in order to effect vaporization of the alcohol and thereby permit recovery of alcohol vapors 172 from this flashing zone. A lean solvent phase comprising the carboxylic acid extraction solvent can be withdrawn from flashing zone 170 via conduit 166 and recycled to extraction zone 160, after addition of make-up carboxylic acid extraction solvent 169, if required.

The conditions of temperature and pressure which are employed in flashing zone 170 for alcohol recovery will vary widely depending upon the alcohol to be recovered, the particular carboxylic acid extraction solvent which is used, and other factors. Generally, however, the flashing zone 170 should employ a temperature of from about 30° to 150° C., preferably from about 60° to 120° C., for recovery of alcohols of from 2 to 8 carbon atoms. Preferably, the carboxylic acid extraction solvent which is used in this invention, when such a flashing method of alcohol recovery is to be used, possesses a normal boiling point of at least 100°, more preferably at least 140°, greater than the normal boiling point of the alcohol in order to permit more efficient separation of the alcohol vapors 172 without, at the same time, contaminating the thus-separated vapors with significant quantities of the carboxylic acid solvent itself.

The conditions of pressure which are used in flashing zone 170 will, of course, have an effect on the necessary temperatures to recover the alcohol by flashing, but generally, the pressure in the flashing zone 172, will range from about 2 to 150 psia, and more preferably from about 5 to 50 psia.

By this flashing means, introduction of steam into the alcohol-carboxylic acid mixture is prevented. Such steam introduction is undesired since it has been observed that the carboxylic acid's affinity for water is greatly increased in the absence of sulfuric acid. Thus, if open steam distillation or steam stripping were used, while alcohol vapors could be stripped overhead, the bottoms stream from such a steam stripper would comprise an aqueous carboxylic acid mixture which when recycled to the liquid/liquid extraction zone would tend to build water in the system, and decrease the efficiency of reconcentration of sulfuric acid as discussed above. Since low selectivity for water absorbtion by the carboxylic acid solvent in the liquid/liquid extraction zone 160 is critical, the introduction of steam by a steam distillation or a steam stripping process is not preferred. Also, it has been found that alcohol-water-carboxylic acid extraction solvent mixtures can present settling problems in recovering alcohol and/or the carboxylic acid solvent therefrom, when such steam distillation methods are attempted.

The manner in which the acid/alcohol feedstream 104 is formed is not critical to this invention. When feedstream 104 is formed by absorption of olefin into a strong acid, any of the prior art methods and absorption apparatus can be used, as described above.

Therefore, in one embodiment of the process of this invention, feedstream 104 can be formed by passing an olefin stream 102 to conventional absorbing zone 110 for countercurrent contact therein with a concentrated strong acid stream 106. Olefin 102 can comprise any of the above mentioned aliphatic olefins having from 3 to 8 carbon atoms per molecule, and particularly olefins having 3 or 4 carbon atoms per molecule. Similarly, the identity and concentration of the strong acid in acid stream 106, the temperature and pressure and other conditions used in absorbing zone 110 correspond to those which have been discussed earlier. Therefore, when the olefin comprises propylene, and the strong acid is sulfuric acid, stream 106 will generally comprise sulfuric acid of an acid strength of from about 45 to 99%, more preferably from about 50 to 80%, and when the olefin 102 comprises butylene or higher olefin feeds, stream 106 will generally comprise sulfuric acid of an acid strength of from about 45 to 85 wt.% and more preferably from about 55 to 80 wt.%. Generally, a temperature of from about 20° to 150° C. and a pressure of from about 60 to 500 psig wll be used.

Further, any of the above-discussed strong acids can be employed, and such acids will generally comprise a strong organic or inorganic acid which is miscible with water and which is characterized by dissociation constants ("pK" values) in aqueous solutions of less than about 3.5. Examples of suitable inorganic olefin hydration acids are hydrofluoric acid, hydroiodic acid, hydrochloric acid, ortho-phosphoric acid, phosphorous acid, perchloric acid, sulfuric acid and the like. Sulfuric acid is especially preferred. Examples of suitable organic olefin hydration acids re chloroacetic acid, benzene sulfonic acid and the like.

Unabsorbed gases are withdrawn from the upper portion of absorbing zone 110 via conduit 107 and can be recycled if desired to conduit 102 or subjected to conventional scrubbing/washing treatment, as with caustic solutions.

Therefore, the alcohols recovered by the process of this invention comprise the alcohol corresponding to the olefin(s) fed to the absorbing zone 110, and generally comprise saturated mono-alcohols having from 3 to 8 carbon atoms per molecule, and preferably having 3 or 4 carbon atoms per molecule. Examples of such alcohols are n-butanol, iso-butanol, sec-butanol, tert-butyl alcohol, n-propanol, iso-propanol, pentanols, hexanols and octanols.

As used herein, the term "extract saturation" (i.e., "E.S." values) of strong acid solutions, containing alcohol and/or alkyl ester of the strong acid, is defined by the expression (III):

$$E.S. = \frac{X^1}{X^4} \qquad (III)$$

wherein $X^1$ is the mole fraction of alcohol (and alcohol-equivalents represented by the alkyl esters) absorbed in the liquid and $X^4$ is the mole fraction in the liquid of the strong acid and strong acid moieties of the strong acid esters.

In the Examples, sulfuric acid concentrations are expressed as "acid strength", i.e., "A.S." values (defined above), unless otherwise indicated.

EXAMPLE 1

A mixture of butene, secondary butyl ether ("SBE"), sec-butyl alcohol ("SBOH"), butyl ester of sulfuric acid ("BuHSO4") sulfuric acid, and water was prepared in the selected amounts and passed as an acid/alcohol feedstream (having an acid strength of 55 wt.% $H_2SO_4$ and an extract saturation value of 1.0) to the upper portion of a continuous Karr extraction unit comprising a reciprocating plate column (total liquid holdup equals 650 cc.) and contacted therein with a selected amount of neo-decanoic acid which was passed to the reciprocating plate column at the lower portion thereof. The liquids thus passed to the extraction unit were preheated each to a temperature of 60° C. The reciprocating plate column was provided with a hot water heating jacket maintained at 60° C. The upper portion of the extraction unit column was provided with a phase separator whereby a "light phase", comprising the neodecanoic acid and extracted sec-butyl alcohol values, were accumulated and withdrawn for analysis. From the bottom portion of the column, a "heavy phase", comprising the alcohol depleted sulfuric acid stream, was also withdrawn and collected, for analysis. The liquids thereby accumulated were each analyzed by gas chromatography and nuclear magnetic resonance spectroscopy (NMR) for component identification. The heavy phase was found to have a 60-percent acid strength, compared to the 55-percent acid strength of the feedstream to the extraction column.

The data thereby obtained are set forth in Table I.

TABLE 1

Continuous Extraction[1]
Solvent = neo-decanoic acid

| Components | Acid/Alcohol Feedstream[2] GMS | Feed Rate Moles | Solvent[3] GMS | Feed Rate Moles | Light Phase GMS | Feed Rate Moles | Heavy Phase GMS | Feed Rate Moles | Overall Partition coefficients Wt. Fract.[4] |
|---|---|---|---|---|---|---|---|---|---|
| Butene | 0.268 | 0.005 | 0 | 0 | 1.38 | 0.025 | 0.011 | 0.0001 | 43.88 |
| SBE | 0.011 | ~0 | 0 | 0 | 0.128 | 0.001 | 0.0035 | ~0 | 12.79 |
| SBOH | 34.35 | 0.464 | 0 | 0 | 25.62 | 0.346 | 7.113 | 0.096 | 1.26 |
| BuHSO$_4$ | 1.138 | 0.007 | 0 | 0 | 0 | 0 | 0.073 | 0.0004 | 0 |
| H$_2$SO$_4$ | 45.97 | 0.469 | 0 | 0 | 0.051 | 0.0005 | 46.60 | 0.475 | 0.0004 |
| Water | 29.86 | 1.659 | 0.068 | 0.004 | 1.100 | 0.0611 | 29.21 | 1.623 | 0.0132 |
| Solvent | 0 | 0 | 227.7 | 1.324 | 227.6 | 1.323 | 0.109 | 0.0006 | 730.3 |
| Total | 111.6 | 2.605 | 227.8 | 1.328 | 255.9 | 1.757 | 89.5 | 2.196 | — |

[1] Column residence time = 3.52 hours. Solvent-to-feed weight ratio = 2.04:1. Feed rates expressed as mole/½ hour.
[2] Feed: E.S. = 1; A.S. = 55%; specific gravity, 25° C. = 1.21; Temp. = 60° C.
[3] Solvent = neo-decanoic acid (Exxon Chemical Americas, >95% purity)
[4] Calculated from component's concentration in light phase ÷ its concentration in heavy phase.

EXAMPLE 2

The procedure of Example 1 was repeated, employing the feedstream and other conditions indicated in Table 2 below.

EXAMPLE 3

The procedure of Example 1 was repeated employing the feedstream and other conditions indicated in Table 3 below.

EXAMPLE 4

The procedure of Example 1 was repeated employing the feedstream and other conditions indicated in Table 4 below.

EXAMPLE 5

The procedure of Example 1 was repeated employing the feedstream and other conditions indicated in Table 5 below.

EXAMPLE 6

The procedure of Example 1 was repeated employing the feedstream and other conditions indicated in Table 6 below.

EXAMPLE 7

The procedure of Example 1 was repeated employing the feedstream and other conditions indicated in Table 7 below.

TABLE 2

Continuous Extraction[2]
Solvent = Neo-decanoic Acid

| Components | Acid/Alcohol Feedstream[2] GMS | Feed Rate Moles | Solvent[3] GMS | Feed Rate Moles | Light Phase GMS | Feed Rate Moles | Heavy Phase GMS | Feed Rate Moles | Overall Partition Coefficients Wt. Fract.[4] |
|---|---|---|---|---|---|---|---|---|---|
| Butene | 0.130 | .002 | 0 | 0 | 0.583 | 0.010 | ~0 | ~0 | 2000+ |
| SBE | 0.011 | ~0 | 0 | 0 | 0.0253 | 0.0001 | 0.0001 | ~0 | 81.2 |
| SBOH | 33.80 | 0.467 | 0 | 0 | 23.93 | 0.323 | 9.253 | 0.125 | 0.83 |
| BuHSO$_4$ | 0.771 | 0.005 | 0 | 0 | 0.253 | 0.002 | 0.071 | 0.0004 | 1.14 |
| H$_2$SO$_4$ | 44.95 | 0.459 | 0 | 0 | 0 | 0 | 45.23 | 0.461 | 0 |
| Water | 28.94 | 1.608 | 0.068 | 0.004 | 1.039 | 0.058 | 28.12 | 1.562 | 0.012 |
| Solvent | 0 | 0 | 227.7 | 1.324 | 227.65 | 1.323 | 0.081 | 0.0004 | 902.5 |
| Total | 108.6 | 2.531 | 227.8 | 1.328 | 253.5 | 1.717 | 81.4 | 2.1496 | — |

[1] Column residence time = 3.62. Solvent-to-feed weight ratio = 2.098:1. Feed rates expressed as mole/½ hour.
[2] Feed: E.S. = 1; A.S. = 55%; specific gravity, 25° C. = 1.21; Temp. = 60° C.
[3] Solvent = neo-decanoic acid (Exxon Chemical Americas, >95% purity).
[4] Calculated from component's concentration in light phase ÷ its concentration in heavy phase.

TABLE 3

Continuous Extraction[1]
Solvent = neo-decanoic acid

| Components | Acid/Alcohol Feedstream[2] GMS | Feed Rate Moles | Solvent[3] GMS | Feed Rate Moles | Light Phase GMS | Feed Rate Moles | Heavy Phase GMS | Feed Rate Moles | Overall Partition Coefficients Wt. Fract.[4] |
|---|---|---|---|---|---|---|---|---|---|
| Butene | 0.258 | 0.005 | 0 | 0 | 1.332 | 0.024 | 0.009 | 0.0001 | 47.09 |
| SBE | 0.0107 | ~0 | 0 | 0 | 0.123 | 0.0009 | 0.003 | ~0 | 13.05 |
| SBOH | 33.088 | 0.447 | 0 | 0 | 24.697 | 0.334 | 6.828 | 0.092 | 1.15 |
| BuHSO$_4$ | 1.0965 | 0.007 | 0 | 0 | 0 | 0 | 0.070 | 0.0004 | 0 |
| H$_2$SO$_4$ | 44.28 | 0.452 | 0 | 0 | 0.049 | 0.0005 | 41.88 | 0.458 | 0.0004 |
| Water | 28.77 | 1.598 | 0.0658 | 0.0036 | 1.061 | 0.059 | 28.14 | 1.563 | 0.012 |
| Solvent | 0 | 0 | 219.5 | 1.276 | 219.5 | 1.276 | 0.0677 | 0.0003 | 1031.7 |

TABLE 3-continued

Continuous Extraction[1]
Solvent = neo-decanoic acid

| Components | Acid/Alcohol Feedstream[2] GMS | Feed Rate Moles | Solvent[3] GMS | Feed Rate Moles | Light Phase GMS | Feed Rate Moles | Heavy Phase GMS | Feed Rate Moles | Overall Partition Coefficients Wt. Fract.[4] |
|---|---|---|---|---|---|---|---|---|---|
| Total | 107.5 | 2.509 | 219.6 | 1.280 | 246.7 | 1.694 | 78.5 | 2.114 | — |

[1]Column residence time = 3.66 hours. Solvent-to-feed weight ratio = 2.043:1. Feed rates expressed as mole/½ hr
[2]Feed: E.S. = 1; A.S. = 55%; specific gravity, 25° C. = 1.21; Temp. = 60° C.
[3]Solvent = neo-decanoic acid (Exxon Chemical Americas, >95% purity)
[4]Calculated from component's concentration in light phase ÷ its concentration in heavy phase.

TABLE 4

| Components | Acid/Alcohol Feedstream[2] GMS | Feed Rate Moles | Solvent[3] GMS | Feed Rate Moles | Light Phase GMS | Feed Rate Moles | Heavy Phase GMS | Feed Rate Moles | Overall Partition Coefficients Wt. Fract.[4] |
|---|---|---|---|---|---|---|---|---|---|
| Butene | 0.0115 | 0.0002 | 0 | 0 | 0.998 | 0.018 | 0.0004 | ~0 | 944.6 |
| SBE | 0.0115 | ~0 | 0 | 0 | 0.026 | 0.0002 | 0.004 | ~0 | 2.46 |
| SBOH | 20.42 | 0.276 | 0 | 0 | 17.617 | 0.238 | 1.479 | 0.02 | 4.51 |
| BuHSO4 | 0.530 | 0.003 | 0 | 0 | 0 | 0 | 0.086 | 0.0005 | 0 |
| H2SO4 | 54.46 | 0.556 | 0 | 0 | 0.0525 | 0.0005 | 54.69 | 0.558 | 0.004 |
| Water | 39.87 | 2.215 | 0.073 | 0.004 | 0.709 | 0.039 | 39.553 | 2.197 | 0.007 |
| Solvent | 0 | 0 | 243.2 | 1.414 | 243.1 | 1.414 | 0.0794 | 0.0004 | 1159.1 |
| Total | 115.3 | 3.050 | 243.3 | 1.418 | 262.55 | 1.710 | 99.4 | 2.776 | — |

[1]Column residence time = 3.66 hrs. Solvent-to-feed weight ratio = 2.11:1. Solvent feed temp. = 30° C. Feed rates expressed as mole/½ hour.
[2]Feed: E.S. = 1; A.S. = 55%; specific gravity, 25° C. = 1.21; Temp. = 60° C.
[3]Solvent = neodecanoic acid (Exxon Chemical Americas, >95% purity).
[4]Calculated from component's concentration in light phase ÷ its concentration in heavy phase.

TABLE 5

| Components | Acid/Alcohol Feedstream[2] GMS | Feed Rate Moles | Solvent[3] GMS | Feed Rate Moles | Light Phase GMS | Feed Rate Moles | Heavy Phase GMS | Feed Rate Moles | Overall Partition Coefficients Wt. Fract.[4] |
|---|---|---|---|---|---|---|---|---|---|
| Butene | 0.14 | 0.002 | 0 | 0 | 0.18 | 0.003 | 0.0002 | ~0 | 496.3 |
| SBE | 0.012 | ~0 | 0 | 0 | 0.098 | 0.0007 | 0.0001 | ~0 | 540.4 |
| SBOH | 36.285 | 0.49 | 0 | 0 | 19.232 | 0.2598 | 16.90 | 0.228 | .627 |
| BuHSO4 | 0.828 | 0.005 | 0 | 0 | ~0 | ~0 | 0.076 | 0.0004 | — |
| H2SO4 | 48.26 | 0.492 | 0 | 0 | 0.163 | 0.001 | 48.635 | 0.496 | 0.002 |
| Water | 31.07 | 1.726 | 0.043 | 0.002 | 0.866 | 0.048 | 30.275 | 1.682 | 0.016 |
| Solvent | 0 | 0 | 142.95 | 0.8311 | 142.86 | 0.8305 | 0.096 | 0.0005 | 820.6 |
| Total | 116.6 | 2.717 | 143. | 0.834 | 163.4 | 1.144 | 90.1 | 2.408 | — |

[1]Column residence time = 3.37 hrs. solvent-to-feed weight ratio = 1.23:1. Feed rates expressed as mole/½ hr.
[2]Feed: E.S. = 1; A.S. = 55%; specific gravity = 1.21; Temp. = 60° C.
[3]Solvent = neo-decanoic acid (Exxon Chemical Americas, >95% purity).
[4]Calculated from component's concentration in light phase ÷ its concentration in heavy phase.

TABLE 6

| Components | Acid/Alcohol Feedstream[2] GMS | Feed Rate Moles | Solvent[3] GMS | Feed Rate Moles | Light Phase GMS | Feed Rate Moles | Heavy Phase GMS | Feed Rate Moles | Overall Partition Coefficients Wt. Fract.[4] |
|---|---|---|---|---|---|---|---|---|---|
| Butene | 0.066 | 0.001 | 0 | 0 | 0.491 | 0.009 | 0.0002 | ~0 | 904.7 |
| SBE | 0.033 | 0.0002 | 0 | 0 | 0.123 | 0.0009 | 0.0001 | ~0 | 453.3 |
| SBOH | 35.97 | 0.486 | 0 | 0 | 16.95 | 0.229 | 18.356 | 0.248 | 0.340 |
| BuHSO4 | 2.358 | 0.015 | 0 | 0 | 0.245 | 0.0015 | 0.072 | 0.0004 | 1.254 |
| H2SO4 | 44.61 | 0.455 | 0 | 0 | 0 | 0 | 45.91 | 0.468 | 0 |
| Water | 27.16 | 1.509 | 0.680 | 0.004 | 0.736 | 0.041 | 26.64 | 1.480 | 0.010 |
| Solvent | 0 | 0 | 226.83 | 1.318 | 226.75 | 1.318 | 0.0766 | 0.0004 | 1090.9 |
| Total | 110.2 | 2.467 | 226.9 | 1.322 | 245.3 | 1.60 | 90.4 | 2.198 | — |

[1]Column residence time = 3.60 hrs solvent-to-feed weight ratio = 2.06:1. Feed rates expressed as mole/½hr.
[2]Feed: E.S. = 1; A.S. = 60%; specific gravity = 1.22. Temp. = 60° C.
[3]Solvent = neo-decanoic acid (Exxon Chemical Americas, >95% purity).
[4]Calculated from component's concentration ratios in light phase ÷ its concentration in heavy phase.

TABLE 7

| Components | Acid/Alcohol Feedstream[2] GMS | Feed Rate Moles | Solvent[3] GMS | Feed Rate Moles | Light Phase GMS | Feed Rate Moles | Heavy Phase GMS | Feed Rate Moles | Overall Partition Coefficients Wt. Fract.[4] |
|---|---|---|---|---|---|---|---|---|---|
| Butene | 0.063 | 0.001 | 0 | 0 | 0.265 | 0.005 | 0.0002 | ~0 | 808.6 |

TABLE 7-continued

| Components | Acid/Alcohol Feedstream[2] GMS | Acid/Alcohol Feedstream[2] Feed Rate Moles | Solvent[3] GMS | Solvent[3] Feed Rate Moles | Light Phase GMS | Light Phase Feed Rate Moles | Heavy Phase GMS | Heavy Phase Feed Rate Moles | Overall Partition Coefficients Wt. Fract.[4] |
|---|---|---|---|---|---|---|---|---|---|
| SBE | 0.032 | 0.0002 | 0 | 0 | 0.172 | 0.001 | 0.00012 | ~0 | 874.7 |
| SBOH | 34.30 | 0.464 | 0 | 0 | 10.31 | 0.139 | 23.57 | 0.318 | 0.267 |
| BuHSO$_4$ | 2.249 | 0.015 | 0 | 0 | 0.156 | 0.001 | 0.069 | 0.0004 | 1.38 |
| H$_2$SO$_4$ | 42.54 | 0.434 | 0 | 0 | 0 | 0 | 43.83 | 0.447 | 0 |
| Water | 25.91 | 1.439 | 0.043 | 0.002 | 0.406 | 0.022 | 25.63 | 1.434 | 0.010 |
| Solvent | 0 | 0 | 144.75 | 0.842 | 144.7 | 0.841 | 0.0665 | 0.0003 | 1327.9 |
| Total | 105.1 | 2.353 | 144.8 | 0.844 | 156. | 1.010 | 95.2 | 2.190 | — |

[1]Column residence time = 3.77 hrs. Solvent-to-feed weight ratio = 1.38:1. Feed rates expressed as mole/½hr.
[2]Feed: E.S. = 1; A.S. = 60 wt. %; specific gravity = 1.22; Temp = 60° C.
[3]Solvent = neo-decanoic acid (Exxon Chemical Americas, >95% purity).
[4]Calculated from component's concentration ratios in light phase ÷ its concentration in heavy phase.

Batchwise Preparation of Acid/Alcohol Feedstreams Containing Absorbed Olefin

A sulfuric acid stream containing absorbed butylene values was prepared by charging 400 cc. of sulfuric acid of the selected strength (from 50 to 75 wt.% H$_2$SO$_4$) to a one liter baffled Hastelloy C autoclave equipped with a flat blade turbine stirrer and an olefin gas sparger for sparging directly into the liquid phase under the stirrer. The autoclave was also provided with thermocouples to measure the liquid reaction medium temperature, and was provided with an electric heating mantle and cold water cooling coil for temperature control. After the charged sulfuric acid was heated to the selected reaction temperature, the butylene gas feed, preheated to the reaction temperature, was sparged to the liquid sulfuric acid at the selected gas feed rate. Unabsorbed gases were continuously withdrawn from the autoclave, and the absorbed butylene was accumulated in the reactor until the desired extract saturation (ES value) was obtained.

Thereafter, the thus-formed acid/alcohol feedstreams are contacted with the selected amount of a carboxylic acid solvent of this invention, and the results thereby obtained are reported in the associated tables below.

EXAMPLE 8

The above batchwise procedure for preparing an acid/alcohol feedstream was followed to obtain an ES value of 0.5 and sulfuric acid A.S. value of 56.7%. In a series of runs, separate portions of the acid/alcohol feedstreams were contacted with the indicated amount of octanoic acid for extraction of sec-butyl alcohol (SBA) therefrom using the indicated contacting temperatures, employing a 60 ml. separatory funnel, with agitation, and employing 3 hours of setting time. The weight percent sec-butyl alcohol in the light phase (i.e., the upper layer comprising the octanoic acid layer) was then analyzed. The data thereby obtained are set forth in Table 8 below.

TABLE 8

Effect of Temperature and Feed Ratio on SBA Extraction Using Octanoic Acid As Solvent

| Run No. | Contacting Temp. °C. | v:v Ratio Solvent:Acid/ Alcohol Feedstream | SBA in Light Phase wt. % |
|---|---|---|---|
| 8-1 | 60 | 1.0 | 9.91 |
| 8-2 | 60 | 2.0 | 7.20 |
| 8-3 | 25 | 0.2 | 7.38 |
| 8-4 | 25 | 0.4 | 7.57 |
| 8-5 | 25 | 1.0 | 6.15 |
| 8-6 | 25 | 1.5 | 5.37 |

TABLE 8-continued

Effect of Temperature and Feed Ratio on SBA Extraction Using Octanoic Acid As Solvent

| Run No. | Contacting Temp. °C. | v:v Ratio Solvent:Acid/ Alcohol Feedstream | SBA in Light Phase wt. % |
|---|---|---|---|
| 8-7 | 25 | 2.0 | 4.54 |

EXAMPLE 9

The procedure of Example 8 was repeated employing the indicated contacting temperatures and employing either octanoic acid, neoheptanoic acid or neo decanoic acid as solvent. The data thereby obtained are set forth in Table 9 below.

TABLE 9

Extraction Efficiency of Aliphatic Acids

| Run No. | Contacting Temp (°C.) | Extraction Solvent[1] | SBA in Light Phase wt. % |
|---|---|---|---|
| 9-1 | 60 | octanoic acid | 9.91 |
| 9-2 | 25 | octanoic acid | 6.15 |
| 9-3 | 60 | neoheptanoic acid | 7.82 |
| 9-4 | 25 | neoheptanoic acid | 5.04 |
| 9-5 | 60 | neodecanoic acid | 6.44 |
| 9-6 | 25 | neodecanoic acid | 4.04 |

[1]Vol:vol ratio = 1.0:1, solvent:acid/alcohol feedstream. (Acid/alcohol feedstream AS = 56.7%; ES = 0.5).

EXAMPLE 10

The procedure of Example 9 was repeated except that the solvent/feed ratio for each extraction solvent of this invention was varied to determine the effect of solvent to feed ratio on the selectivity of extraction, such extraction selectivity being determined as the weight ratio of water to secondary butyl alcohol in the upper layer. All runs were conducted using a 25° C. contacting temperature, an A.S. value of 56.7% and an extract saturation value of 0.5. The data thereby obtained are set forth in Table 10.

These data indicate that solvent to feed ratio has a pronounced, non-linear effect on the selectivity for alcohol extraction, with increasing amounts of water being removed together with the acid solvent, for example, in the case of octanoic acid, as the solvent to feed ratio is increased above about 0.5. In contrast, a high selectivity for alcohol extraction (and, concurrently the lower selectivity for water removal) is achieved using neoheptanoic and neodecanoic acids at solvent to feed ratios of from 1.0:1 to 2.0:1 (vol:vol).

TABLE 10
Effect of Solvent/Feed Ratio on H₂O/SBA With Various Aliphatic Acids

| Run No. | Solvent | Solvent/Feed (v/v) | wt:wt. ratio $H_2O$/SBA In Upper Layer |
|---|---|---|---|
| 10-1 | neoheptanoic acid | 0.2 | — |
| 10-2 | neoheptanoic acid | 0.4 | 0.099 |
| 10-3 | neoheptanoic acid | 1.0 | 0.054 |
| 10-4 | neoheptanoic acid | 1.5 | 0.045 |
| 10-5 | neoheptanoic acid | 2.0 | 0.067 |
| 10-6 | octanoic acid | 0.2 | 0.066 |
| 10-7 | octanoic acid | 0.4 | 0.055 |
| 10-8 | octanoic acid | 1.0 | 0.067 |
| 10-9 | octanoic acid | 2.0 | 0.101 |
| 10-10 | octanoic acid | 0.2 | 0.079 |
| 10-11 | neodecanoic acid | 0.4 | 0.077 |
| 10-12 | neodecanoic acid | 1.0 | 0.030 |
| 10-13 | neodecanoic acid | 1.5 | 0.023 |
| 10-14 | neodecanoic acid | 2.0 | 0.038 |

EXAMPLE 11

The procedure of Example 8 was repeated in a series of runs employing an extract saturation value of 1.0 and a solvent to feed ratio (volume to volume basis) of 1:1, using neodecanoic acid as the extraction solvent, and employing sulfuric acid of the selected acid strength, at two contacting temperature conditions, in order to determine the effect of acid strength on the alcohol capacity of the neodecanoic acid. The results thereby obtained are set forth in Table 11.

Therefore, it has been found that the capacity for alcohol removal of neodecanoic acid was greatly increased at both the 25° C. and 60° C. contacting temperatures by decreasing the weight percent sulfuric acid in the acid/alcohol feedstreams. The data in Table 11 also indicate that increasing acid strengths resulted in a greatly increased amount of butylene regenerated in the upper layer containing the neo-decanoic acid solvent, particularly when the acid/alcohol feedstream has an A.S. value of greater than about 60%. Therefore, it can be seen that if the acid strength of the acid/alchol feedstream is not greater than about 60% A.S., then the regenerated olefin in the light phase will comprise less than about 5 wt.% of the alcohol present in the acid/alcohol feedstream treated by use of the process of this invention. In contrast, conventional stream stripping methods for alcohol recovery from an absorber product stream generally result in regenerated olefin of above 15-25 wt.% of the alcohol contained in the absorber product stream.

TABLE 11
Effect of Acid Strength on the Efficiency of SBA Removal by Neodecanoic Acid

| Run No. | Temperature (°C.) | Acid/Alcohol Feedstream AS % | Light Phase SBA wt. % | Regenerated Olefin wt:wt $C_4^=$/SBA |
|---|---|---|---|---|
| 11-1 | 25 | 50 | 11.69 | 0.003 |
| 11-2 | 25 | 60 | 4.57 | 0.013 |
| 11-3 | 25 | 67.5 | 1.79 | 0.165 |
| 11-4 | 60 | 50 | 13.40 | 0.060 |
| 11-5 | 60 | 60 | 7.11 | 0.049 |
| 11-6 | 60 | 67.5 | 3.55 | 0.161 |

EXAMPLE 12

A series of runs were made using the procedure of Example 8, in which the weight percent sulfuric acid content (i.e., the acid strength) and the extract saturation values of a series of acid/alcohol feedstreams was varied, Each feedstream was contacted with neodecanoic acid (vol:vol 1:1) at a contacting temperature of 25° C. The concentration of neodecanoic acid in a heavy phase was then determined to assess the solubility of neo-decanoic acid therein as a function of extract saturation values. The data thereby obtained are set forth in Table 12. From these data it can be seen that, at each acid strength level tested, the solubility of neo-decanoic acid in the heavy phase (which comprise the depleted sulfuric acid solution) increases as the ES value of the feed extract increases, and that best results were obtained (that is lowest concentration of the neodecanoic acid in the heavy layer were achieved) when the ES value in the feed extract was less than about 0.4.

TABLE 12
Solubility of Neodecanoic Acid in SBOH Extracts

| Sample No. | Acid/Alcohol Feedstream Acid Strength (AS Value) % | E.S. Value | Neodecanoic Acid in Heavy Layer (ppm by weight) |
|---|---|---|---|
| 1 | 56.7 | 0 | Not detectable |
| 2 | 56.7 | 0.1 | <10 |
| 3 | 56.7 | 0.2 | 17 |
| 4 | 56.7 | 0.3 | 157 |
| 5 | 56.7 | 0.4 | 364 |
| 6 | 56.7 | 0.5 | 571 |
| 7 | 56.7 | 1.0 | 4776 |
| 8 | 67.0 | 0 | 9 |
| 9 | 67.0 | 0.2 | 785 |
| 10 | 67.0 | 0.6 | 1855 |
| 11 | 67.0 | 1.0 | 9887 |

*at 25° C.

EXAMPLE 13

The following example will serve to illustrate another advantage of the process of this invention, viz. the lower quantity of water required to dilute the acid/alcohol feedstream for recovery of the desired alcohol.

Referring to FIG. 1, the prior art method of alcohol recovery, it can be shown by calculations that an absorber product stream 4 having an acid strength (AS) of 71% and an extract saturation (ES) value of 1.2 (and therefore comprising 47.75 wt.% $H_2SO_4$, 32.74 wt.% butylene-equivalents and 19.51 wt.% water) requires 19.56 grams of additional water be added, per 100 grams of the absorber product stream 4, in order to reduce the acid concentration to an acid strength (A.S.) of 55%. The subsequent steam stripping of this diluted acid stream for alcohol recovery provides a depleted sulfuric acid stream which must be reconcentrated to 71% A.S. before recycle to the absorber 10.

In contrast, referring to FIG. 2, the process of the present invention, to achieve a 55% A.S. after addition of water 112 to the same absorber product stream 104, can efficiently recover the alcohol using a 60% A.S. and ES of 1.0 in the absorber product stream, and only about 6.8 grams of water, per 100 grams of absorber product stream 104, is required to be added in diluting this stream to the desired 55% A.S. level.

EXAMPLES 14-21

The following runs were made to illustrate our discovery of a major and unexpected difference in solution behavior in the partitioning of alcohol into a neo-acid extraction solvent of this invention from aqueous alcohol, neo-acid mixtures free of sulfuric acid as compared to that observed for such mixtures which also comprise sulfuric acid.

A series of extractions were performed using the method of Example 8 upon acid/alcohol feedstreams prepared as in Example 8, using the sulfuric acid concentrations, butylene concentrations and other conditions set forth in Tables 13 and 14 below, which also summarizes the data thereby obtained.

As can be seen from Tables 13 and 14 the extent of removal of water from the alcohol-containing feeds using neodecanoic acid as the extraction solvent was surprisingly far less when the feed comprised aqueous sec-butanol/sulfuric acid mixtures (Examples 14–21) than when the feed comprised aqueous sec-butanol alone (Comparative Examples I-IX).

then shaken for 10 seconds to thoroughly mix the liquid phases. The shaking was stopped and the liquid mixture was observed to determine the time required to form a liquid-liquid interface between the upper phase (the alcohol-containing neo-decanoic acid extract phase) and the lower phase (the alcohol-depleted sulfuric acid phase). These times are reported as "break times" in Table 15 below.

As can be seen from Table 15, the extraction runs in which the carboxylic acid extraction solvent comprised the continuous liquid phase (Runs 1-B through 6-B) effected a breaktime greatly decreased from those observed in Runs 1-A through 6-A, respectively, for the extractions in which the carboxylic acid extraction solvent comprised the dispersed liquid phase, that is the discontinuous liquid phase. Therefore, the extraction

TABLE 13

Neodecanoic Acid - Solvent

| Example No. | Acid/Alcohol Feedstream | | | | | NDA/SBOH wt:wt Ratio[1] | Light Phase[2] | | Overall Partition Coeff. SBOH[3] |
|---|---|---|---|---|---|---|---|---|---|
| | ES Value | AS (%) | Total GMS | SBOH Content Gms | Solvent Gms | | [$H_2O$] wt % | [SBOH] wt % | |
| 14 | 0.2 | 60 | 13.93 | 1.133 | 17.72 | 15.6 | .12 | 1.89 | 0.3 |
| 15 | 0.2 | 60 | 27.93 | 2.271 | 8.94 | 3.9 | .10 | 2.49 | 0.35 |
| 16 | 0.2 | 60 | 13.90 | 1.130 | 8.84 | 7.9 | .10 | 2.22 | 0.33 |
| 17 | 0.2 | 60 | 13.81 | 1.123 | 26.23 | 23.2 | .09 | 1.65 | 0.31 |
| 18 | 0.2 | 60 | 26.46 | 1.89 | 8.90 | 4.7 | .34 | 6.68 | 1.35 |
| 19 | 1.0 | 60 | 23.72 | 6.80 | 8.94 | 1.3 | .66 | 6.87 | 0.25 |
| 20 | 1.0 | 60 | 11.84 | 3.39 | 8.90 | 2.6 | .47 | 6.06 | 0.24 |
| 21 | 1.0 | 60 | 11.85 | 3.40 | 26.8 | 7.9 | .38 | 5.15 | 0.34 |

Notes:
[1] wt:wt ratio of SBOH and NDA charged.
[2] Light phase = NDA/SBOH extract phase.
[3] SBOH Partition Coefficient = SBOH concentration in light phase ÷ SBOH concentration in heavy phase.
SBOH = sec-butyl alcohol; NDA = neodecanoic acid.
Temperature of extraction = 60° C.

TABLE 14

Comparative Runs, NDA = Solvent

| Comparative Example No. | Starting SBOH Mixture | | | Solvent GMS | Light Phase[1] | | | Heavy Phase[2] | | | Overall Partition Coeff.[3] SBOH |
|---|---|---|---|---|---|---|---|---|---|---|---|
| | GMS | SBOH (wt %) | $H_2O$ (wt %) | | GMS | SBOH (wt %) | $H_2O$ (wt %) | GMS | SBOH (wt %) | $H_2O$ (wt %) | |
| I | 16.93 | 47.8 | 52.2 | 26.08 | 35.43 | 22.15 | 3.02 | 8.18 | 5.44 | 94.56 | 4.1 |
| II | 21.57 | 7.3 | 92.7 | 69.26 | 71.11 | 2.07 | 0.63 | 19.72 | 0.94 | 99.06 | 2.2 |
| III | 27.7 | 63.9 | 36.1 | 63.00 | 80.45 | 19.57 | 2.59 | 10.24 | 4.91 | 95.09 | 4.0 |
| IV | 11.62 | 13.9 | 86.1 | 78.64 | 80.67 | 2.01 | 0.59 | 9.57 | 0.90 | 99.02 | 2.2 |
| V | 17.47 | 45.3 | 54.7 | 27.28 | 36.23 | 20.65 | 2.45 | 8.52 | 3.44 | 96.56 | 6.0 |
| VI | 21.49 | 7.4 | 92.6 | 68.24 | 70.50 | 2.16 | 1.14 | 19.23 | 0.49 | 99.51 | 4.4 |
| VII | 25.75 | 61.7 | 38.3 | 62.05 | 79.05 | 19.72 | 3.33 | 8.75 | 3.08 | 96.92 | 6.4 |
| VIII | 11.44 | 13.5 | 86.5 | 78.76 | 80.5 | 1.89 | 0.95 | 9.7 | 0.42 | 99.58 | 4.5 |
| IX | 29.52 | 28.3 | 71.7 | 65.46 | 35.65 | 10.53 | 2.74 | 9.31 | 1.75 | 98.25 | 6.0 |

Notes:
SBOH = sec-butyl alcohol; NDA = neo-decanoic acid
[1] Light phase = SBOH + $H_2O$ + NDA (Balance).
[2] Heavy phase = SBOH + $H_2O$ = NDA (Balance).
[3] Extraction Temperatures: 25° C. (Comp. Examples I-IV); 60° C. (Comp. Examples V-IX).

EXAMPLE 22

A series of experiments were performed to illustrate the benefits found in practice of the process of this invention by contacting the acid/alcohol feedstream with a carboxylic acid extraction solvent of this invention in a manner in which the acid/alcohol feedstream comprised the discontinuous phase in the extraction zone. A 150 cc glass tube was charged with 60 cc of a mixture comprising the selected proportion of an aqueous sulfuric acid solution of the indicated A.S. and E.S. values, containing sec-butyl alcohol, and neo-decanoic acid, as the extraction solvent. The mixture was heated to a temperature of 60° C. (at atmospheric pressure) by heating the glass tube in an oil bath, and the mixture was process of this invention is preferably performed in a manner in which the acid/alcohol feedstream is the discontinuous liquid phase in the extraction zone.

TABLE 15

| Run No. | Acid/Alcohol Feedstream | | | NDA Solvent | Breaktime (Sec.) |
|---|---|---|---|---|---|
| | A.S. (%) | E.S. | Vol. %[1] | Vol. %[1] | |
| 1-A | 55 | 0.51 | 60 | 40 | 170 |
| 1-B | " | " | 40 | 60 | 120 |
| 2-A | " | 0.97 | 60 | 40 | 260 |
| 2-B | " | " | 40 | 60 | 50 |
| 3-A | " | 1.13 | 60 | 40 | 300 |
| 3-B | " | " | 40 | 60 | 40 |

TABLE 15-continued

| Run No. | Acid/Alcohol Feedstream | | | NDA Solvent | Breaktime (Sec.) |
|---|---|---|---|---|---|
| | A.S. (%) | E.S. | Vol. %[1] | Vol. %[1] | |
| 4-A | 60 | 0.51 | 60 | 40 | 195 |
| 4-B | " | " | 40 | 60 | 130 |
| 5-A | " | 0.97 | 60 | 40 | 160 |
| 5-B | " | " | 40 | 60 | 50 |
| 6-A | " | 1.13 | 60 | 40 | 225 |
| 6-B | " | " | 40 | 60 | 50 |

Notes:
NDA = Neodecanoic acid
[1]Vol. % expressed based on volumes charged to the glass tube.

It will be understood from the foregoing that while the alcohol-recovery method of this invention has been particularly described with regard to alcohol recovery from acid/alcohol feedstreams produced by absorbing olefins into concentrated strong acids, the method of this invention may be employed for recovery of alcohol from such acid/alcohol, mixtures produced by different processes, either as product or by-product streams.

It will be obvious that various changes and modifications may be made without departing from the invention and it is intended, therefore, that all matter contained in the foregoing description shall be interpreted as illustrative only and not limitative of the invention.

What is claimed is:

1. An improved process for recovering aliphatic monoalcohols having from 3 to 8 carbon atoms per molecule from acid/alcohol feedstreams comprising 40 to 80% acid strength strong acid solutions containing said alcohols which comprises (a) contacting said acid/alcohol feedstream in an extraction zone with an effective amount of an extraction solvent selected from the group consisting of alicyclic and acyclic alkyl carboxylic acids having from 6 to 20 carbons per molecule and mixtures thereof, for a time and under conditions sufficient to selectively extract said alcohol from said acid/alcohol feedstream and to form a first liquid phase comprising an alcohol-enriched carboxylic acid extract, and a second liquid phase comprising an aqueous strong acid raffinate depleted in alcohol, and (b) recovering said alcohol-enriched carboxylic acid extract.

2. The process of claim 1 wherein said strong acid comprises sulfuric acid.

3. The process of claim 1 wherein said carboxylic acid extraction solvent comprises at least one acid of the formula: $RCO_2H$, wherein R is an acyclic alkyl group having from 5 to 19 carbon atoms.

4. The process of claim 1 wherein said acid/alcohol feedstream is obtained by the steps of absorbing an olefin corresponding to said alcohol in an aqueous strong acid under conditions sufficient to form said alcohol and an alkyl ester of said strong acid, wherein said alkyl moiety corresponds to said olefin.

5. The process of claim 1 wherein said acid/alcohol stream also contains an alkyl ester of said strong acid, wherein said alkyl moiety corresponds to said alcohol, and wherein said acid/alcohol feedstream is admixed with from about 0.04 to 0.4 parts by weight of water per part by weight of said acid/alcohol feedstream prior to said extraction zone.

6. The process of claim 1 wherein said alcohol-enriched carboxylic acid extract contains less than 1 wt.% of said strong acid.

7. The process of claim 1 wherein said alcohol-enriched carboxylic acid extract contains less than about 2 wt.% water.

8. The process of claim 1 wherein said aqueous strong acid raffinate depleted in alcohol contains said strong acid in an acid strength of at least 1 wt.% greater than the acid strength of said strong acid in said acid/alcohol feedstream introduced to said extraction zone.

9. The process of claim 6 wherein said strong acid strength in said raffinate is from about 2 to 7 wt.% greater than the acid strength of said acid/alcohol feedstream introduced to said extraction zone.

10. The process of claim 1 wherein said alcohol-enriched carboxylic acid extract contains said alcohol in a concentration of from 5 to 20 wt.%.

11. The process of claim 1 wherein said carboxylic acid is a neo-acid selected from the group consisting of acids of the formula

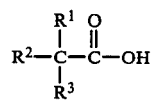

wherein $R^1$, $R^2$ and $R^3$ are the same or different and are independently selected from the group consisting of alkyl of from 1 to 16 carbon atoms.

12. The process of claim 11 wherein $R^1$ and $R^2$ are each alkyl groups having from 1 to 3 carbon atoms per alkyl group, and $R^3$ is alkyl of from 1 to 6 carbon atoms.

13. The process of claim 1 wherein said carboxylic acid extraction solvent is employed in said extraction zone in an amount of from about 0.3 to 5 parts by weight per part by weight of said acid/alcohol feedstream.

14. A process for recovering alcohols from said/alcohol feedstreams comprising 40 to 80% acid strength sulfuric acid solutions containing from about 5 to 50 wt.% of at least one saturated monoalcohol having from 3 to 8 carbon atoms per molecule and from about 1 to 15 wt.% of at least one alkyl ester of sulfuric acid, wherein said alkyl moiety corresponds to said alcohol, which comprises (a) admixing with said acid/alcohol feedstream an amount of water of from about 0.04 to 0.4 parts by weight of water per part by weight of said acid/alcohol feedstream to form a partially diluted acid/alcohol feedstream, (b) contacting said partially diluted acid/alcohol feedstream in an extraction zone with an effective amount of an extraction solvent selected from the group consisting of neo-acids having from 6 to 20 carbon atoms per molecule for a time and under conditions sufficient to selectively extract said alcohol from said partially diluted feedstream and to form a first liquid phase comprising an alcohol-enriched carboxylic acid extract containing said alcohol in a concentration of from about 5 to 20 wt% and a second liquid phase comprising an aqueous sulfuric acid raffinate depleted in alcohol and having a sulfuric acid strength of at least 1 wt.% greater than the sulfur acid strength in said partially diluted acid/alcohol feedstream, and (c) recovering said alcohol-enriched carboxylic acid extract.

15. The process of claim 14 wherein said neo-acid extraction solvent is employed in said extraction zone in an amount of from about 0.3 to 5 parts by weight of said neo-acid per part by weight of said partially diluted acid/alcohol feedstream.

16. The process of claim 14 wherein said alcohol-enriched carboxylic acid extract contains less than about 2 wt.% water and less than about 1 wt.% sulfuric acid.

17. The process of claim 1 wherein said alcohol comprises at least one member selected from the group consisting of iso-propanol, secondary-butanol and tertiary-butanol.

18. The process of claim 14 wherein said neo acid comprises at least one member selected from the group consisting of 2,2-dimethyl butanoic acid; alpha, alpha dimethylcyclohexyl acetic acid; alpha, alpha dimethyl octanoic acid; 1-methyl-4-propylcyclohexane-1-carboxylic acid; neo-heptanoic acid, neo-octanoic acid, neo-nonanoic acid, neo-decanoic acid and neo-tridecanoic acid.

19. The process of claim 1 wherein said extraction zone comprises a continuous counter-current extraction zone and wherein said neo-acid extraction solvent comprises the continuous phase and said acid/alcohol feedstream comprises the discontinuous phase in said extraction zone.

20. The process of claim 11 wherein said neo-acid comprises at least one member selected from the group consisting of 2,2-dimethyl butanoic acid; alpha, alpha dimethylcyclohexyl acetic acid; alpha, alpha-dimethyl octanoic acid; 1-methyl-4-propylcyclohexane-1-carboxylic acid; neo-heptanoic acid; neo-octanoic acid; neo-nonanoic acid; neo-decanoic acid; and neo-tridecanoic acid.

* * * * *